April 12, 1955 V. E. HOLMES Plant Pat. 1,377
ROSE PLANT
Filed July 13, 1954
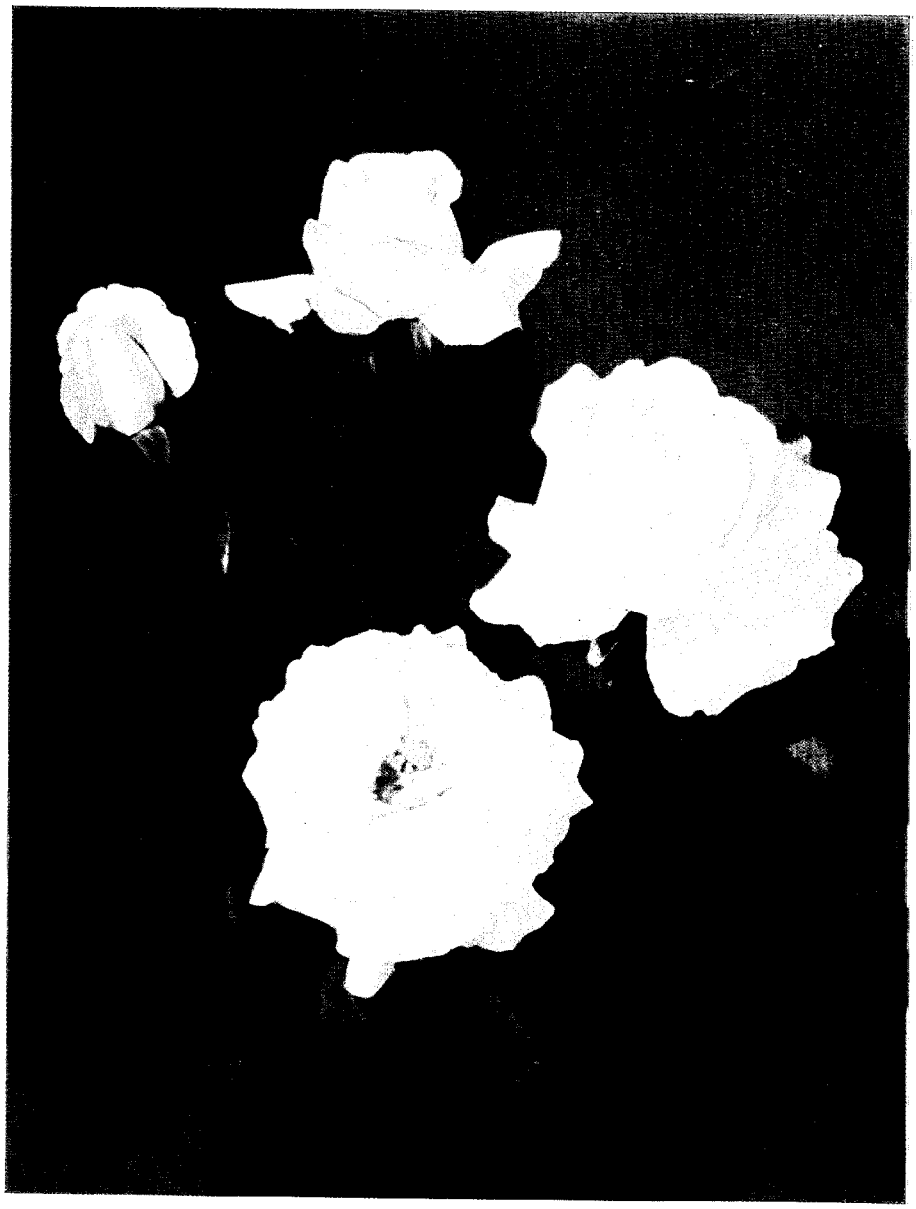
INVENTOR
Victor E. Holmes
By Orville M. Kile
Plant Pat. Agt.

United States Patent Office

Plant Pat. 1,377
Patented Apr. 12, 1955

1,377

ROSE PLANT

Victor E. Holmes, San Bruno, Calif., assignor to Avansino-Mortensen & Company, San Bruno, Calif.

Application July 13, 1954, Serial No. 443,190

1 Claim. (Cl. 47—61)

My present discovery relates to a white sport of the German polyantha rose known as Rosenelfe or Rose Elfe (unpatented). It was discovered by me at the San Bruno, California, rose range of the company of which I am part owner, in the course of my usual duties of looking out for new and unusual plants. Asexual reproduction by me by means of budding, grafts and cuttings at our San Leandro rose range, through several generations, has shown its qualities to be firmly fixed.

The principal difference between the new variety and its parent lies in the flower color, although the two varieties also differ in other respects—notably that the new variety has greater flower petalage and petal substance, as well as more vigor of growth.

Illustrations accompanying this specification are color photographs of several specimens of the bud and flower of my new variety in different stages of opening, together with portions of stems and foliage—all in approximately their true colors.

Following is a detailed description of the plant and flower of my new variety, in which color plate numbers refer to Ridgway's Color Standards and Nomenclature.

THE PLANT

Growth: Bushy. Very vigorous, growing to a height of 5 or 6 feet as a bench rose and 2 to 3 feet when grown outside. It is extremely "free-breaking."

Blooming habit: Very prolific bloomer. Under glass it is a continuous bloomer throughout the year. Outside it has three or four main crops in the season from April to October, although some blooms can be found all the year in this climate.

Borne: Singly and in umbel-like clusters of from three to about seven.

Stems:

*Color.*—Approximately Light Elm Green (Pl. XVII). New wood red-tinged.

*Type.*—Straight, strong and heavy. Internodes medium length.

*Thorns.*—Large, sharp, outward-pointing, red-tinged.

Foliage:

*Leaves.*—Mostly 3 to 5 leaflets.

*Color.*—Dark, approximately Elm Green (Pl. XVII) on upper surface and Bice Green (Pl. XVII) on under surface. New foliage approximately Neutral Red (Pl. XXXVIII).

*Size.*—Large. Terminal leaflet usually 2½ to 3 inches long by 1¾ to 2 inches wide. First set of laterals often almost as large as terminal leaflet.

*Shape.*—Oval, with rounded base and sharply pointed apex. Edge evenly and shallowly serrated.

*Texture.*—Leathery.

*Stipules.*—Small and clinging.

*Rachis.*—Heavy. Grooved above and smooth below except for an occasional small thorn.

*Aspect.*—Veining inconspicuous, giving leaf a flat appearance.

THE FLOWER

Bud:

*Size.*—When first showing color, approximately ½ inch long above the receptacle.

*Shape.*—Young bud is pointed, with calyx hooded above it. When calyx spreads and bud begins to open, it is blunt. As the bud opens, the outer petals reflex, leaving the center pointed but with the spreading petals beginning to reflex.

*Opening.*—Slow.

*Sepals.*—Short and mostly simple.

*Peduncle.*—Strong, straight, relatively short, slightly lighter than stems. Covered with fine spines.

*Color.*—Pure white except for greenish tinge at base which spreads upward through the veins. Occasional bud has splotch of rose color on outer surface of one or two of its petals.

Bloom:

*Size.*—Medium, measuring 2 to 2½ inches across when fully open.

*Form.*—Full, with pointed center and reflexed outer petals until fully open. Then it becomes deeply cup-shaped. Stamens remain covered until the very last stages of opening.

*Petalage.*—Double. Number of petals varies but averages about 40 to 45.

*Longevity.*—Good.

*Fragrance.*—Slight.

*Color.*—Outer petals white with light yellowish-green tinge at base. As the flower opens the inner petals show a very slight soft pink tinge—much too pale to designate by plate number but of the pale Cameo Pink (Pl. XXVI) type. When the flower opens completely the entire rose has this faint pink tinge, although the rose is still essentially a white one. As in the bud, occasionally there is a splotch of rose color on the outer surface of one or two of the petals but it is not then visible.

Petals:

*Size.*—Outer petals are about 1¼ inches long; slightly narrower than that at the top and considerably narrower at the base.

*Shape.*—Obcordate. Edges reflexed, particularly in the early stages of opening.

*Texture.*—Substantial.

*Persistence.*—Clinging.

Reproductive organs:

*Pistils.*—Many; tightly bunched in center of flower. *Styles* slender, short, and greenish-white. *Stigmas* greenish-white.

*Stamens.*—Surround pistils. Filaments greenish-white; irregular in length. Anthers medium in size; dark yellow, approximately Yellow Ocher (Pl. XV).

Having thus disclosed my discovery, I claim:

The new and distinct variety of polyantha rose plant, substantially as herein shown and described, characterized particularly by its essentially white flowers with extremely pale pink tinge; its vigorous growth and prolific blooming habits; and the larger petalage and better substance of its flowers as compared with the parent variety.

No references cited.